(12) United States Patent
Madera et al.

(10) Patent No.: US 6,635,658 B2
(45) Date of Patent: Oct. 21, 2003

(54) AMINO-TETRALIN DERIVATIVES AS MUSCARINIC RECEPTOR ANTAGONISTS

(75) Inventors: Ann Marie Madera, Dublin, CA (US); Robert James Weikert, Boulder Creek, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/308,092

(22) Filed: Dec. 2, 2002

(65) Prior Publication Data

US 2003/0171362 A1 Sep. 11, 2003

Related U.S. Application Data

(60) Provisional application No. 60/336,675, filed on Dec. 3, 2001.

(51) Int. Cl.⁷ .................. A61K 31/4468; C07D 211/58
(52) U.S. Cl. ........................ 514/319; 546/223; 546/214; 546/189; 544/129; 544/360; 514/235.5; 514/252; 514/255; 514/316; 514/326
(58) Field of Search .................. 514/319, 326, 514/316, 255, 252, 235.5; 546/223, 214, 189; 544/360, 129

(56) References Cited

U.S. PATENT DOCUMENTS

| | | | |
|---|---|---|---|
| 5,026,857 A | * | 6/1991 | Schohe et al. ............ 514/319 |
| 5,179,108 A | | 1/1993 | George et al. |
| 6,319,920 B1 | | 11/2001 | Caroon et al. |
| 2002/0004494 A1 | | 1/2002 | Weikant et al. |
| 2002/0004501 A1 | | 1/2002 | Dvorak et al. |

FOREIGN PATENT DOCUMENTS

| | | |
|---|---|---|
| EP | 0270947 B1 | 5/1993 |
| FR | 2 659 853 A1 | 9/1991 |
| WO | WO 89/09050 A1 | 10/1989 |
| WO | WO 98/01425 A1 | 1/1998 |
| WO | WO 01/90082 A1 | 11/2001 |

* cited by examiner

*Primary Examiner*—Charanjit S. Aulakh
(74) *Attorney, Agent, or Firm*—Rohan Peries; Brian Buckwalter

(57) ABSTRACT

This invention relates to compounds which are generally muscarinic M2/M3 receptor antagonists and which are represented by Formula I:

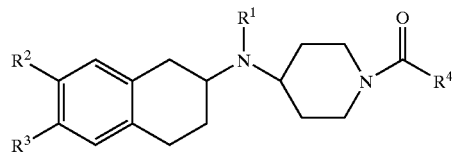

wherein $R^1$, $R^2$, $R^3$ and $R^4$ are as defined in the specification, or individual isomers, racemic or non-racemic mixtures of isomers, or acceptable salts or solvates thereof. The invention further relates to pharmaceutical compositions containing such compounds and methods for their use and preparation as therapeutic drugs.

45 Claims, No Drawings

AMINO-TETRALIN DERIVATIVES AS MUSCARINIC RECEPTOR ANTAGONISTS

CROSS-REFERENCE

This application claims the benefit of priority of U.S. Provisional Patent Application Serial No. 60/336,675, filed Dec. 3, 2001, which is incorporated herein by reference in its entirety.

FIELD OF THE INVENTION

This invention relates to amino-tetralin derivatives, associated acceptable salts, or hydrates thereof, and associated compositions and methods for use as M2/M3 selective muscarinic receptor antagonists.

BACKGROUND OF THE INVENTION

Acetylcholine (Ach) is the principal transmitter of the parasympathetic nervous system. The physiological actions of Ach are mediated by activation of either nicotinic or muscarinic receptors. Both of these receptor classes are heterogeneous: e.g., the muscarinic receptor family comprises five subtypes ($M_1$, $M_2$, $M_3$, $M_4$, and $M_5$) each encoded by distinct genes and possessing unique pharmacology and distribution.

Almost all smooth muscle tissues express both muscarinic M2 and M3 receptors, both of which have a functional role. M2 receptors outnumber M3 receptors by a proportion of approximately 4 to 1. Generally, M3 receptors mediate the direct contractile effects of acetylcholine in the vast majority of smooth muscle tissues. M2 receptors, on the other hand, cause smooth muscle contraction indirectly by inhibiting sympathetically (β-adrenoreceptor)-mediated relaxation.

Compounds that act as antagonists of muscarinic receptors have been used to treat several disease states associated with improper smooth muscle function, as well as in the treatment of cognitive and neurodegenerative disorders such as Alzheimer's disease. Until recently, most of these compounds have been non-selective for the various muscarinic receptor subtypes, leading to unpleasant anti-cholinergic side-effects such as dry mouth, constipation, blurred vision, or tachycardia. The most common of these side-effects is dry-mouth resulting from muscarinic receptor blockade in the salivary gland. Recently developed M2 or M3 specific antagonists have been shown to have reduced side effects. Evidence suggests that mechanistically, concurrent blockade of M2 and M3 receptors could be therapeutically effective in the treatment of disease states associated with smooth muscle disorders.

Additionally, muscarinic receptor antagonists are front-line therapy as bronchodilators in chronic obstructive pulmonary disease (COPD). It is thought that the efficacy of this class of molecules is mediated through antagonism of the natural transmitter (acetylcholine) at M3 receptors on airway smooth muscle and there may be additional benefit in COPD through inhibition of mucus secretion which may also be mediated through M3 receptors. The current standard anti-muscarinic for the treatment of COPD is ipratropium (Atrovent) which is administered by aerosol 4 times per day. More recently tiotropium (Spiriva) has been developed by Boehringer-Ingelheim as a second-generation muscarinic antagonist and is expected to be launched in 2002 (in collaboration with Pfizer). Tiotropium is also given by aerosol but has a slow off-rate from the M3 receptor and, as a result, causes a prolonged bronchodilatation. Tiotropium will be given once per day. Although tiotropium has high affinity for all muscarinic receptor subtypes, it is a quaternary ammonium compound which is poorly absorbed.

Few M2/M3 selective antagonists have been developed. The present invention fills this need by providing these types of antagonists useful in the treatment of disease states associated with improper smooth muscle function and respiratory disorders.

SUMMARY OF THE INVENTION

This invention relates to compounds comprising Formula I:

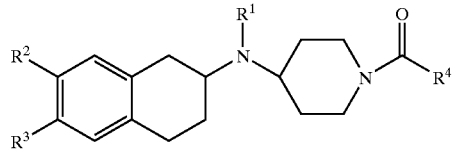

Formula I wherein:
$R^1$ is ($C_{1-6}$)alkyl;
$R^2$ is halogen or —OR';
$R^3$ is hydrogen or —OR';
R' is hydrogen, ($C_{1-6}$)alkyl, or $SO_2R''$;
R" is ($C_{1-6}$)alkyl, haloalkyl, aryl or heteroaryl, wherein said aryl or heteroaryl groups are optionally substituted with a group selected from ($C_{1-6}$)alkyl, halo, haloalkyl, cyano, nitro, alkylsulfonyl, and alkylsulfonylamino,
$R^4$ is ($C_{1-6}$)alkyl, aryl, heterocyclyl, or heteroaryl, wherein said aryl, heterocyclyl or heteroaryl groups are optionally substituted with a group selected from ($C_{1-6}$) alkyl, halo, haloalkyl, ($C_{1-6}$)alkoxy, cyano, amino, mono- or di alkylamino, nitro, alkylsulfonyl, alkylcarbonyl, urea, alkylcarbonylamino, alkylsulfonylamino, alkylaminosulfonyl, alkoxycarbonyl, heterocyclyl and heteroaryl, or —$NR^5R^6$; and
$R^5$ and $R^6$ are independently of each other hydrogen, ($C_{1-6}$)alkyl, aryl or heterocyclyl; wherein said aryl or heterocyclyl groups are optionally substituted with ($C_{1-6}$)alkyl, halo, haloalkyl, cyano, ($C_{1-6}$)alkoxy, and alkylsulfonyl,
or prodrugs, individual isomers, racemic or non-racemic mixtures of isomers, or salts or solvates thereof.

In preferred embodiments $R^2$ is ($C_{1-6}$)alkoxy, hydroxy or —$OSO_2R''$ wherein R" is ($C_{1-6}$)alkyl, haloalkyl, aryl or heteroaryl, and $R^3$ is hydrogen or ($C_{1-6}$)alkyl; in another preferred embodiment $R^2$ is ($C_{1-6}$)alkoxy and $R^3$ is hydrogen, and in another preferred embodiment $R^2$ and $R^3$ are ($C_{1-6}$)alkoxy.

In another preferred embodiment $R^4$ is ($C_{1-6}$)alkyl, and within this embodiment other preferred group of compounds is that wherein $R^1$ is ethyl or propyl.

In another preferred embodiment $R^4$ is an aryl group; and in another preferred embodiment $R^4$ is phenyl optionally substituted with a group selected from ($C_{1-6}$)alkyl, halo, haloalkyl, ($C_{1-6}$)alkoxy, cyano, amino, mono- or di alkylamino, nitro, alkylsulfonyl, alkylcarbonyl, urea, alkylcarbonylamino, alkylsulfonylamino, alkylaminosulfonyl, alkoxycarbonyl, heterocyclyl and heteroaryl, and within this embodiment other preferred group of compounds is that wherein $R^1$ is ethyl or propyl. Another preferred group of compounds is that wherein $R^2$ is —OR', and $R^3$ is —OR' or hydrogen.

In another preferred embodiment $R^4$ is a heteroaryl group; and in another preferred embodiment $R^4$ is selected from furanyl, thiophenyl, isooxazolyl, oxazolyl, imidazolyl, and pyrazolyl, all optionally substituted with one or two $(C_{1-6})$ alkyl, and within this embodiment another preferred group of compounds is that wherein $R^1$ is ethyl or propyl, and another preferred group of compounds is that wherein $R^2$ is —OR', and $R^3$ is —OR' or hydrogen.

In another preferred embodiment $R^4$ is a heterocyclyl group; and in another preferred embodiment $R^4$ is piperidinyl, pyrrolidinyl, morpholinyl, piperazinyl, diazepanyl, all optionally substituted with one or two $(C_{1-6})$ alkyl or alkylcarbonyl groups, and within this embodiment another preferred group of compounds is that wherein $R^1$ is ethyl or propyl, and another preferred group of compounds is that wherein $R^2$ is —OR', and $R^3$ is —OR' or hydrogen.

In another preferred embodiment $R^4$ is —$NR^5R^6$, and $R^5$ is $(C_{1-6})$alkyl and $R^6$ is hydrogen or $(C_{1-6})$alkyl; and in another preferred embodiment $R^4$ is —$NR^5R^6$, $R^5$ is heterocyclyl and $R^6$ is hydrogen, and within this embodiment another preferred group of compounds is that wherein $R^1$ is ethyl or propyl, and another preferred group of compounds is that wherein $R^2$ is —OR', and $R^3$ is —OR' or hydrogen.

In another aspect, the invention relates to pharmaceutical compositions containing a therapeutically effective amount of at least one compound of Formula I, or individual isomers, racemic or non-racemic mixtures of isomers and salts or solvates thereof, in admixture with at least one suitable carrier.

In another aspect, this invention relates to a method of treatment of a disease in a mammal treatable by administration of at least one compound of Formula I, having selective activity for the M2 and M3 muscarinic receptors, in particular a method of treatment in a subject having a disease state comprising smooth muscle disorders; preferably genitourinary tract disorders, respiratory tract disorders, gastrointestinal tract disorders; more preferably genitourinary tract disorders such as overactive bladder or detrusor hyperactivity and its symptoms, such as the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity and the like; and the symptoms usually manifested in detrusor hyperreflexia (neurogenic bladder), in conditions such as outlet obstruction, outlet insufficiency, pelvic hypersensitivity, or in idiopathic conditions such as detrusor instability, and the like. In another preferred embodiment, the disease comprises respiratory tract disorders such as allergies and asthma. In another preferred embodiment, the disease state comprises gastrointestinal disorders.

In another aspect, the invention relates to a process for preparing a compound of Formula I, which process comprises reacting a compound having a general formula d:

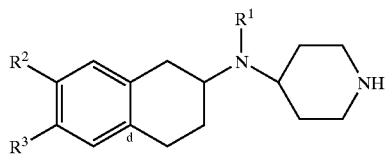

wherein $R^1$, $R^2$, and $R^3$ are as described in the summary of the invention, with a compound of formula $R^4C(O)L$, wherein L is a leaving group and $R^4$ is as described in the summary of the invention, to give a compound of Formula I:

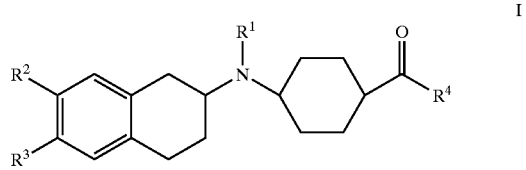

wherein $R^1$, $R^2$, $R^3$ and $R^4$ are as described in the summary of the invention.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an", and "the" include plural referents unless the context clearly dictates otherwise.

"Alkyl" means the monovalent linear or branched saturated hydrocarbon radical, having from one to six carbon atoms inclusive, unless otherwise indicated. Examples of alkyl radicals include, but are not limited to, methyl, ethyl, propyl, isopropyl, 1-ethylpropyl, sec-butyl, tert-butyl, n-butyl, n-pentyl, n-hexyl, and the like. "Aryl" means the monovalent aromatic carbocyclic radical consisting of one individual ring, or one or more fused rings in which at least one ring is aromatic in nature, which can optionally be substituted with one or more, preferably one or two, substituents selected from hydroxy, cyano, $(C_{1-6})$alkyl, $(C_{1-6})$alkoxy, haloalkoxy, alkylthio, halo, haloalkyl, hydroxyalkyl, nitro, cyano, alkoxycarbonyl, amino, alkylamino, alkylsulfonyl, alkylcarbonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, alkylaminocarbonyl, arylcarbonylamino, heterocyclyl, heteroaryl, and urea, unless otherwise indicated. Alternatively two adjacent atoms of the aryl ring may be substituted with a methylenedioxy or ethylenedioxy group. Examples of aryl radicals include, but are not limited to, phenyl, naphthyl, biphenyl, indanyl, anthraquinolyl, tert-butyl-phenyl, 1,3-benzodioxolyl, o-tolyl, trifluoromethylphenyl, methanesulfonylphenyl, ureaphenyl, pyrrolydinylphenyl, tetrazolylphenyl, and the like.

"Heteroaryl" means the monovalent aromatic cyclic radical having one or more rings, preferably one to three rings, of four to eight atoms per ring, incorporating one or more heteroatoms, preferably one or two, within the ring (chosen from nitrogen, oxygen, or sulfur), which can optionally be substituted with one or more, preferably one or two substituents selected from hydroxy, cyano, $(C_{1-6})$alkyl, $(C_{1-6})$alkoxy, lower haloalkoxy, alkylthio, halo, haloalkyl, hydroxyalkyl, nitro, cyano, alkoxycarbonyl, amino, alkylamino, alkylcarbonyl, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and urea, unless otherwise indicated. Examples of heteroaryl radicals include, but are not limited to, imidazolyl, oxazolyl, thiazolyl, imidazolyl, pyrazinyl, pyrazolyl, tetrazolyl, thienyl, furanyl, pyridinyl, quinolinyl, isoquinolinyl, benzofuryl, benzothiophenyl, benzothiopyranyl, benzimidazolyl, benzoxazolyl, benzothiazolyl, benzopyranyl, indazolyl, indolyl, isoindolyl, quinolinyl, isoquinolinyl, naphthyridinyl, benezenesulfonyl-thiophenyl, and the like.

"Heterocyclyl" means the monovalent saturated cyclic radical, consisting of one or more rings, preferably one to two rings, of three to eight atoms per ring, incorporating one or more ring heteroatoms (chosen from N, O or $S(O)_{0-2}$), and which can optionally be substituted with one or more, preferably one or two substituents selected from hydroxy, oxo, cyano, $(C_{1-6})$alkyl, $(C_{1-6})$alkoxy, haloalkoxy, alkylthio, halo, haloalkyl, hydroxyalkyl, nitro, cyano, alkoxycarbonyl, amino, alkylamino, alkylsulfonyl, arylsulfonyl, alkylcarbonyl, arylcarbonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and urea unless otherwise indicated. Examples of heterocyclic radicals include, but are not limited to, morpholinyl, piperazinyl, piperidinyl, pyrrolidinyl, tetrahydropyranyl, thiomorpholinyl, 2-oxo-pyrrolidinyl, 3,5-dimethyl-piperazinyl, 4-methylpiperazin-1-yl, 1-methyl-piperidin-4-yl and the like.

"Haloalkyl" means the alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Halogen" means the radical fluoro, bromo, chloro, and/or iodo.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkane- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters. Examples of protecting groups can be found in T. W. Greene et al., *Protective Groups in Organic Chemistry*, (J. Wiley, $2^{nd}$ ed. 1991) and Harrison et al., *Compendium of Synthetic Organic Methods*, Vols. 1–8 (J. Wiley and Sons 1971–1996).

"Amino-protecting group" means the protecting group that refers to those organic groups intended to protect the nitrogen atom against undesirable reactions during synthetic procedures and includes, but is not limited to, benzyl (Bnz), benzyloxycarbonyl (carbobenzyloxy, Cbz), p-methoxybenzyloxycarbonyl, p-nitrobenzyloxycarbonyl, tert-butoxycarbonyl (Boc), trifluoroacetyl, and the like. It is preferred to use either Boc or Cbz as the amino-protecting group because of the relative ease of removal, for example by mild acids in the case of Boc, e.g., trifluoroacetic acid or hydrochloric acid in ethyl acetate; or by catalytic hydrogenation in the case of Cbz.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. 1966, *Angew. Chem. Inter*. Edit., 5, 385; errata 511; Cahn et al. 1966, *Angew. Chem*., 78, 413; Cahn and Ingold 1951, *J. Chem. Soc*. (London), 612; Cahn et al. 1956, *Experientia*. 12, 81; Cahn, J. 1964, *Chem.Educ*., 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

"Substantially pure" means at least about 80 mole percent, more preferably at least about 90 mole percent, and most preferably at least about 95 mole percent of the desired enantiomer or stereoisomer is present.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred acceptable salts are the salts formed from hydrochloric acid, trifluoroacetic acid, dibenzoyl-L-tartaric acid, and phosphoric acid.

It should be understood that all references to acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp.352–401; *Design of Prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like.

"Therapeutically effective amount" means an amount of a compound that, when administered to a subject for treating a disease state, is sufficient to effect such treatment for the disease state. The "therapeutically effective amount" will vary depending on the compound and disease state being treated, the severity of the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Disease state" means any disease, condition, symptom, or indication.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state;

(2) inhibiting the disease state, i.e., arresting the development of the disease state or its clinical symptoms; or (3) relieving the disease state, i.e., causing temporary or permanent regression of the disease state or its clinical symptoms.

"Antagonist" means a molecule such as a compound, a drug, an enzyme inhibitor, or a hormone, that diminishes or prevents the action of another molecule or receptor site.

"Disorders of the urinary tract" or "uropathy" used interchangeably with "symptoms of the urinary tract" means the pathologic changes in the urinary tract. Symptoms of the urinary tract include overactive bladder (also known as detrusor hyperactivity), outlet obstruction, outlet insufficiency, and pelvic hypersensitivity.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy (BPH), urethral stricture disease, tumors and the like. It is usually symptomatically manifested as obstructive (low flow rates, difficulty in initiating urination, and the like) or irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to, pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

Throughout the application the following abbreviations are used with the following meanings:

| Bnz | benzyl |
| --- | --- |
| Boc | ter-butoxycarbonyl |
| BPH | Benign prostatic hypertrophy or benign prostatic hyperplasia |
| DMF | N,N-Dimethylformamide |
| DMSO | Dimethylsulfoxide |
| EDCl | 1-(3-Dimethylaminopropyl)-3-ethylcarbodiimide hydrochloride |

-continued

| EtOAc | Ethyl acetate |
| --- | --- |
| Hal | Halogen or halide |
| HOBT | 1-Hydroxybenzotriazole hydrate |
| Pro | Protective group |
| TFA | Trifluoroacetic acid |
| TFAA | Trifluoroacetic acid anhydride |
| THF | Tetrahydrofuran |

Nomenclature

The naming and numbering of the compounds of this invention is illustrated below:

Formula I

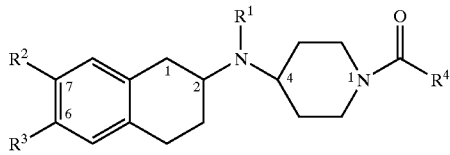

In general, the nomenclature used in this Application is based on AUTONOM™, a Beilstein Institute computerized system for the generation of IUPAC systematic nomenclature.

For example a compound of Formula I wherein $R^1$ is propyl, $R^2$ and $R^3$ are —$OCH_3$, and $R^4$ is 4-methyl-piperazin-1-yl is named: {4-[(6,7-dimethoxy-1,2,3,4-tetrahydro-naphthalen-2-yl)-propyl-amino]-piperidin-1-yl}-(4-methyl-piperazin-1-yl)-methanone.

Preferred Compounds

Among compounds of the present invention set forth in the Summary of the Invention, certain compounds of Formula I, or prodrugs, individual isomers, racemic or non-racemic mixtures of isomers, or acceptable salts or solvates thereof, are preferred:

$R^1$ is preferably ($C_{1-6}$)alkyl, more preferably ethyl and propyl;

$R^2$ is preferably halogen or —OR', more preferably halogen or ($C_{1-6}$)alkoxy;

$R^3$ is preferably hydrogen or —OR', more preferably hydrogen or ($C_{1-6}$)alkoxy;

R' is preferably hydrogen, ($C_{1-6}$)alkyl, or —$SO_2R"$, more preferably ($C_{1-6}$)alkyl, R" is preferably ($C_{1-6}$)alkyl, haloalkyl, aryl or heteroaryl, more preferably aryl or heteroaryl;

$R^4$ is —$NR^5R^6$, aryl, heterocyclyl or heteroaryl, more preferably heterocyclyl or heteroaryl;

$R^5$ and $R^6$ are independently of each other hydrogen, ($C_{1-6}$)alkyl, aryl, or heterocylyl, more preferably ($C_{1-6}$) alkyl or heterocyclyl.

Other preferred compounds of the present invention include the acceptable salts of the compounds of the present invention, wherein the acceptable salts are preferably formed from hydrochloric acid or 2,2,2-trifluoroacetic acid.

Exemplary particularly preferred compounds, or prodrugs, individual isomers, racemic or non-racemic mixtures of isomers, or salts or solvates thereof include:

{4-[(7-methoxy-1,2,3,4-tetrahydro-naphthalen-2-yl)-propyl-amino]-piperidin-1-yl}-piperazin-1-yl-methanone;

{4-[(7-methoxy-1,2,3,4-tetrahydro-naphthalen-2-yl)-propyl-amino]-piperidin-1-yl}-morpholin-4-yl-methanone;

{4-[(6,7-dimethoxy-1,2,3,4-tetrahydro-naphthalen-2-yl)-propyl-amino]-piperidin-1-yl}-piperidin-4-yl-methanone;

{4-[((R)-7-methoxy-1,2,3,4-tetrahydro-naphthalen-2-yl)-propyl-amino]-piperidin-1-yl}-piperidin-4-yl-methanone;

1-{4-[(7-methoxy-1,2,3,4-tetrahydro-naphthalen-2-yl)-propyl-amino]-piperidin-1-yl}-ethanone;

{4-[(6,7-dimethoxy-1,2,3,4-tetrahydro-naphthalen-2-yl)-propyl-amino]-piperidin-1-yl}-piperazin-1-yl-methanone;

{4-[(7-methoxy-1,2,3,4-tetrahydro-naphthalen-2-yl)-propyl-amino]-piperidin-1-yl}-(4-methyl-piperazin-1-yl)-methanone, and {4-[(7-Bromo-1,2,3,4-tetrahydro-naphthalen-2-yl)-propyl-amino]-piperidin-1-yl}-piperidin-4-yl-methanone.

GENERAL SYNTHETIC REACTION SCHEMES

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser 1991 *Reagents for Organic Synthesis*; Wiley & Sons: New York, Volumes 1–15; Rodd 1989 *Chemistry of Carbon Compounds*, Elsevier Science Publishers, Volumes 1–5 and Supplementals; and 1991 *Organic Reactions*, Wiley & Sons: New York, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

SCHEME A

Scheme A, in general describes a method of preparing a compound of Formula I wherein $R^1$, $R^2$, $R^3$, and $R^4$ are as described in the Summary of the invention.

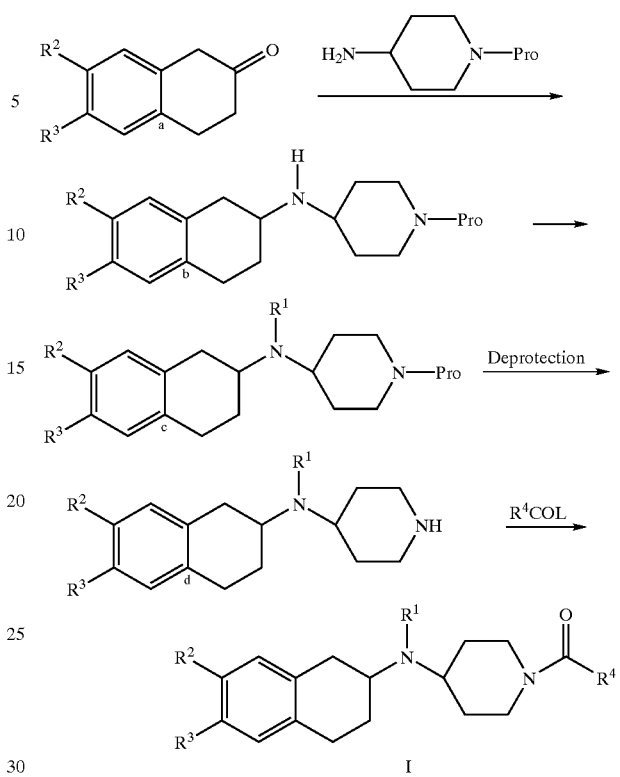

A compound of Formula b, wherein Pro is a protective group, can generally be prepared by coupling a tetralone of Formula a with a protected amino piperidine under reductive amination conditions. Suitable reducing conditions include sodium triacetoxyborohydride, sodium cyanoborohydride, titanium isopropoxide and sodium cyanoborohydride, hydrogen and a metal catalyst and hydrogen transferring agents such as cyclohexene, formic acid and its salts, zinc and hydrochloric acid formic acid or borane sulfide followed by treatment with formic acid. Suitable organic solvents for the reaction include dichloromethane, 1,2-dichloroethane, tetrahydrofuran, alcohols or ethyl acetate, and the like. Preferably the reaction is carried out under basic conditions with sodium triacetoxyborohydride in 1,2-dichloroethane. Reductive amination procedures are described in the chemical literature. For example, *J. Org. Chem.*, 1996, 61, 3849 and *Tetrahedron Letters*, 1996, 37, 3977, describe methods utilizing sodium triacetoxyborohydride as a reagent for the reductive amination of aldehydes with a wide variety of amines. Compound b is further coupled under reductive amination conditions as described herein, with a carboxaldehyde to generally give a compound of Formula c, wherein $R^1$ is as described in the summary of the invention, which after deprotection of the piperidine group under conditions well known in the art as described herein, to give a compound of Formula d, can undergo acylation, with an acid chloride of formula $R^4C(O)L$, wherein L is a leaving group and $R^4$ is as described in the summary of the invention, under conditions well known in the art, to generally give a compound of Formula I.

The conventional starting materials of Scheme A are commercially available or are known to, or can readily be synthesized by those of ordinary skill in the art.

GENERAL UTILITY

Compounds that act as antagonists of muscarinic receptors have been used to treat several disease states associated with improper smooth muscle function as well as in the treatment of cognitive and neurodegenerative disorders such as Alzheimer's disease. Until recently, most of these compounds have been non-selective for the various muscarinic receptor subtypes, leading to unpleasant anti-cholinergic side-effects such as dry mouth, constipation, blurred vision or tachycardia, the most common of which is dry-mouth that results from muscarinic receptor blockade in the salivary gland. Recently developed M2 or M3 specific antagonists have been shown to have reduced side effects. Evidence suggests that mechanistically, concurrent blockade of M2 and M3 receptors could be therapeutically effective in the treatment of disease states associated with smooth muscle disorders, such as genitourinary tract disorders, respiratory tract disorders, gastrointestinal tract disorders, and smooth muscle disorders.

Genitourinary tract disorders treatable with compounds of this invention specifically include overactive bladder or detrusor hyperactivity and its symptoms such as the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

Gastrointestinal tract disorders treatable with compounds of this invention specifically include irritable bowel syndrome, diverticular disease, achalasia, gastrointestinal hypermotility disorders, and diarrhea. Respiratory tract disorders treatable with compounds of this invention specifically include chronic obstructive pulmonary disease, including chronic bronchitis, emphysema, asthma and pulmonary fibrosis.

Compounds with selectivity for the M2 muscarinic receptor have also been shown to be useful in the treatment of cognitive and neurodegenerative diseases such as for example, Alzheimer's disease, as described in J. Med. Chem. 1993, 36, 3734–3737. U.S. Pat. No. 6,294,554 describes muscarinic antagonists for the treatment of cognitive disorders.

These and other therapeutic uses are described, for example, in Goodman & Gilman, 1996 *The Pharmacological Basis of Therapeutics*, ninth edition, McGraw-Hill, New York, Chapter 26:601–616; and Coleman, R. A., 1994, *Pharmacological Reviews*, 46:205–229.

TESTING

The compounds of this invention are muscarinic receptor antagonists. The muscarinic receptor affinity of test compounds can be determined by an in vitro receptor binding assay which utilizes a cell membrane preparation from the Chinese hamster ovary cells expressing the recombinant human muscarinic receptors ($M_1$–$M_5$), and is described in more detail in Example 12.

The muscarinic antagonist properties of the test compounds can be identified by an in vivo assay which determines inhibitory activity against muscarinic receptor mediated saliva secretion in anesthetized rats, and is described in more detail in the Oxotremorine/Pilocarpine-induced salivation (OIS/PIS) model in anesthetized rats, Example 13.

The muscarinic antagonist properties of the test compounds can be identified by an in vivo assay which determines inhibitory activity against muscarinic receptor mediated bladder contraction in anesthetized rats, and is described in more detail in the inhibition of volume-induced contractions assay, Example 14.

The muscarinic antagonist properties of the test compounds can be identified by an in vivo assay which determines inhibitory activity against muscarinic receptor mediated bladder contraction and saliva secretion in anesthetized dogs, and is described in more detail in Example 15.

The muscarinic antagonist properties of the test compounds as anti-bronchoconstriction agents can be identified by an in vivo assay in anesthetized rats as described in more detail in Example 16.

ADMINISTRATION AND PHARMACEUTICAL COMPOSITION

The present invention includes pharmaceutical compositions comprising at least one compound of the present invention, or a prodrug, an individual isomer, a racemic or non-racemic mixture of isomers or an acceptable salt, or solvate thereof together with at least one acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease. In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about ten (10) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents.

Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

The compounds of the present invention can be formulated in transdermal or subcutaneous drug delivery devices. These delivery systems are advantageous when sustained release of the compound is necessary and when patient compliance with a treatment regimen is crucial. Compounds in a transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington, 1995, *The Science and Practice of Pharmacy*, edited by E. W. Martin, Mack Publishing Company, 19th edition, Easton, Pa. Representative pharmaceutical formulations containing a compound of the present invention are described in Examples 5–11.

EXAMPLES

The following preparations and examples are given to enable those skilled in the art to more clearly understand and to practice the present invention. They should not be considered as limiting the scope of the invention, but merely as being illustrative and representative thereof.

Example 1

{4-[(7-Methoxy-1,2,3,4-tetrahydro-naphthalen-2-yl)-propyl-amino]-piperidin-1-yl}-morpholin-4-yl-methanone

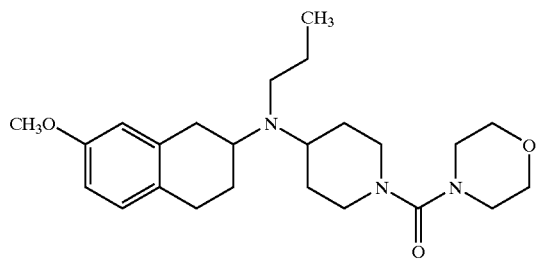

Step 1:
(1-Benzyl-piperidin-4-yl)-(7-methoxy-1,2,3,4-tetrahydro-naphthalen-2-yl)-amine

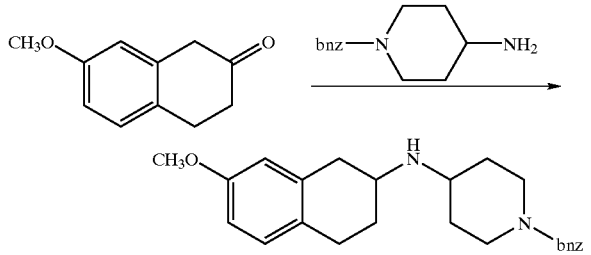

To a solution of 7-methoxy-3,4-dihydro-1H-naphthalen-2-one (10 g, 56.7 mmol) and 1-benzyl-piperidin-4-ylamine (12.7 mL, 62.4 mmol) in dichloroethane (50 mL) under a nitrogen atmosphere was added sodium triacetoxyborohydride (30 g, 141.8 mmol, 3.5 eq.) in a single portion. The reaction was stirred at room temperature for 24 h. The reaction was concentrated in vacuo and partitioned between EtOAc (100 mL) and 5% aq. KOH (50 mL). The aqueous layer was extracted twice more with EtOAc (2×50 mL). The combined organic layers were washed with brine, dried over MgSO$_4$, filtered, and concentrated to afford a dark oil. This material was used directly in Step 2.

Step 2:
(1-Benzyl-piperidin-4-yl)-(7-methoxy-1,2,3,4-tetrahydro-naphthalen-2-yl)-propyl-amine

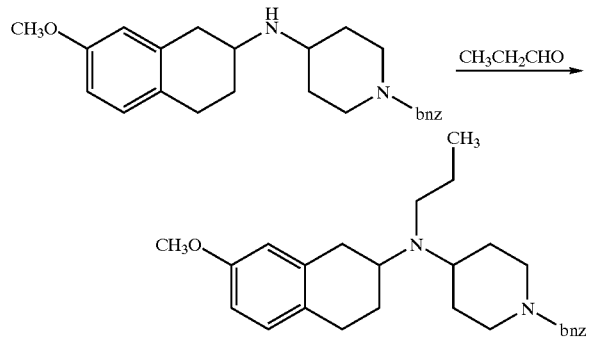

To a solution of (1-benzyl-piperidin-4-yl)-(7-methoxy-1,2,3,4-tetrahydro-naphthalen-2-yl)-amine from Step 1 and propionaldehyde (4.5 mL, 62.4 mmol) in dichloroethane (200 mL) under a nitrogen atmosphere was added sodium triacetoxyborohydride (24 g, 0.113 mol, 2 eq.) in a single portion. The reaction was stirred at room temperature for 24 h then concentrated in vacuo. The residue was partitioned between EtOAc (75 mL) and 5% aq. KOH (50 mL). The aqueous phase was extracted twice more with EtOAc (2×30 mL). The combined organic layers were dried over MgSO$_4$, filtered, and concentrated onto silica (10 g). This was placed on top of a flash column and eluted with 20% hexanes in acetone. The fractions containing product were pooled and concentrated to afford (1-benzyl-piperidin-4-yl)-(7-methoxy-1,2,3,4-tetrahydro-naphthalen-2-yl)-propyl-amine as a clear oil (6.86 g).

Step 3:
(7-Methoxy-1,2,3,4-tetrahydro-naphthalen-2-yl)-piperidin-4-yl-propyl-amine

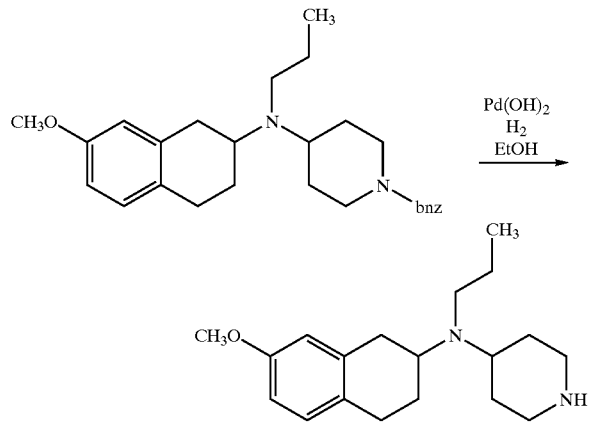

A solution of (1-benzyl-piperidin-4-yl)-(7-methoxy-1,2,3,4-tetrahydro-naphthalen-2-yl)-propyl-amine (6.86 g, 14.47 mmol) in absolute ethanol (100 mL) was poured onto a slurry of 20% Palladium hydroxide/C (1.4 g) in absolute ethanol (10 mL). The mixture was placed under a hydrogen atmosphere on the Parr shaker at 50 psi for 20 h. The reaction mixture was filtered, and concentrated to give (7-methoxy-1,2,3,4-tetrahydro-naphthalen-2-yl)-piperidin-4-yl-propyl-amine (4.2 g).

Step 4a:
{4-[(7-Methoxy-1,2,3,4-tetrahydro-naphthalen-2-yl)-propyl-amino]-piperidin-1-yl}-morpholin-4-yl-methanone

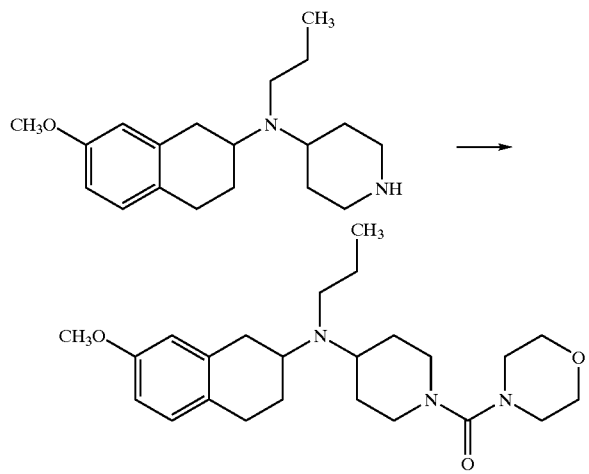

To a solution of (7-methoxy-1,2,3,4-tetrahydro-naphthalen-2-yl)-piperidin-4-yl-propyl-amine (200 μL of 0.025 M in dichloromethane, 50 μmole) was added 200 μL of 0.25 M solution of morpholine 4-carbonyl chloride in dichloromethane and 30 μL of DIEA. The solution was allowed to stir for 24 h at 25° C. under N₂. Concentrated in vacuo. The final product was isolated by preparative RPHPLC (YMC Combiprep ODS-A column, 10–90% acetonitrile: water (0.1% TFA)) to afford {4-[(7-methoxy-1,2,3,4-tetrahydro-naphthalen-2-yl)-propyl-amino]-piperidin-1-yl}-morpholin-4-yl-methanone 1 (11.9 mg), [M+H]⁺=461.

Step 4b:
Alternatively an acid may be used in the last step as an acylating agent. 1-(4-{4-[(7-Methoxy-1,2,3,4-tetrahydro-naphthalen-2-yl)-propyl-amino]-piperidine-1-carbonyl}-piperidin-1-yl)-ethanone

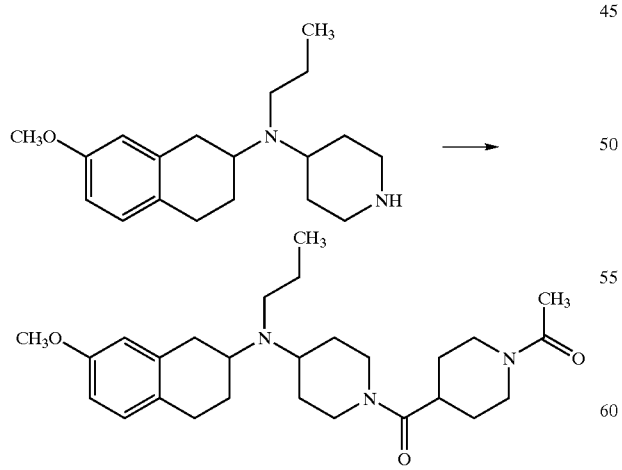

To a solution of (7-methoxy-1,2,3,4-tetrahydro-naphthalen-2-yl)-piperidin-4-yl-propyl-amine (200 μL of 0.25 M in dimethyl formamide, 50 μmole) was added 1-acetylpiperidine-4-carboxylic acid (220 μL of 0.25M in DMF), 300 μL of EDCI (0.25M in DMF) and 220 uL of HOBT (0.25M in DMF) and 30 μL DIEA. The solution was allowed to stir for 48 h at 25° C. under N₂. Concentrated in vacuo. The final product was isolated by preparative RPHPLC (YMC Combiprep ODS-A column, 10–90% acetonitrile: water (0.1% TFA)) to afford 1-(4-{4-[(7-methoxy-1,2,3,4-tetrahydro-naphthalen-2-yl)-propyl-amino]-piperidine-1-carbonyl}-piperidin-1-yl)-ethanone 2 (5.2 mg), [M+H]⁺=456.

Similarly following the procedures described above in Example 1 and using the appropriate acylating compounds in Step 4a or Step 4b, the following compounds were prepared:

{4-[(7-methoxy-1,2,3,4-tetrahydro-naphthalen-2-yl)-propyl-amino]-piperidin-1-yl}-o-tolyl-methanone 3, [M+H]⁺=421;

furan-2-yl-{4-[(7-methoxy-1,2,3,4-tetrahydro-naphthalen-2-yl)-propyl-amino]-piperidin-1-yl}-methanone 4, [M+H]⁺=397;

4-[(7-methoxy-1,2,3,4-tetrahydro-naphthalen-2-yl)-propyl-amino]-piperidine-1-carboxylic acid diethylamide 5, [M+H]⁺=397;

(3,5-dimethyl-isoxazol-4-yl)-{4-[(7-methoxy-1,2,3,4-tetrahydro-naphthalen-2-yl)-propyl-amino]-piperidin-1-yl}-methanone 6, [M+H]⁺=426;

(4-methanesulfonyl-phenyl)-{4-[(7-methoxy-1,2,3,4-tetrahydro-naphthalen-2-yl)-propyl-amino]-piperidin-1-yl}-methanone 7, [M+H]⁺=485;

(4-{4-[(7-methoxy-1,2,3,4-tetrahydro-naphthalen-2-yl)-propyl-amino]-piperidine-1-carbonyl}-phenyl)-urea 8, [M+H]⁺=465;

1-(4-{4-[(7-methoxy-1,2,3,4-tetrahydro-naphthalen-2-yl)-propyl-amino]-piperidine-1-carbonyl}-phenyl)-pyrrolidin-2-one 9, [M+H]⁺=465;

{4-[(7-methoxy-1,2,3,4-tetrahydro-naphthalen-2-yl)-propyl-amino]-piperidin-1-yl}-[4-(1H-tetrazol-5-yl)-phenyl]-methanone 10, [M+H]⁺=475;

N-(4-{4-[(7-methoxy-1,2,3,4-tetrahydro-naphthalen-2-yl)-propyl-amino]-piperidine-1-carbonyl}-phenyl)-methanesulfonamide 11, [M+H]⁺=500;

4-[(7-methoxy-1,2,3,4-tetrahydro-naphthalen-2-yl)-propyl-amino]-piperidine-1-carboxylic acid methylamide 12, [M+H]⁺=360;

4-[(7-methoxy-1,2,3,4-tetrahydro-naphthalen-2-yl)-propyl-amino]-piperidine-1-carboxylic acid (4-trifluoromethyl-phenyl)-amide 13, [M+H]⁺=490;

4-[(7-methoxy-1,2,3,4-tetrahydro-naphthalen-2-yl)-propyl-amino]-piperidine-1-carboxylic acid (3-cyano-phenyl)-amide 14, [M+H]⁺=447;

1-{4-[(7-methoxy-1,2,3,4-tetrahydro-naphthalen-2-yl)-propyl-amino]-piperidin-1-yl}-ethanone 15, [M+H]⁺=381;

{4-[(7-methoxy-1,2,3,4-tetrahydro-naphthalen-2-yl)-propyl-amino]-piperidin-1-yl}-piperazin-1-yl-methanone 16, [M+H]⁺=451;

4-[(7-methoxy-1,2,3,4-tetrahydro-naphthalen-2-yl)-propyl-amino]-piperidine-1-carboxylic acid isopropylamide 17, [M+H]⁺=424;

4-[(7-methoxy-1,2,3,4-tetrahydro-naphthalen-2-yl)-propyl-amino]-piperidine-1-carboxylic acid dimethylamide 18, [M+H]⁺=410;

{4-[(7-methoxy-1,2,3,4-tetrahydro-naphthalen-2-yl)-propyl-amino]-piperidin-1-yl}-piperidin-4-yl-methanone 19, [M+H]⁺=450;

{4-[(7-Methoxy-1,2,3,4-tetrahydro-naphthalen-2-yl)-propyl-amino]-piperidin-1-yl}-(1H-pyrazol-4-yl)-methanone 20, [M+H]⁺=433;

((3R,5S)-3,5-Dimethyl-piperazin-1-yl)-{4-[(7-methoxy-1,2,3,4-tetrahydro-naphthalen-2-yl)-propyl-amino]-piperidin-1-yl}-methanone 21, [M+H]⁺=479;

4-[(7-methoxy-1,2,3,4-tetrahydro-naphthalen-2-yl)-propyl-amino]-piperidine-1-carboxylic acid piperidin-4-ylamide 22, [M+H]⁺=465;

{4-[(7-methoxy-1,2,3,4-tetrahydro-naphthalen-2-yl)-propyl-amino]-piperidin-1-yl}-(4-methyl-piperazin-1-yl)-methanone 23, [M+H]⁺=465;

(1H-imidazol-4-yl)-{4-[(7-methoxy-1,2,3,4-tetrahydro-naphthalen-2-yl)-propyl-amino]-piperidin-1-yl}-methanone 24, [M+H]⁺=433;

[1,4]diazepan-1-yl-{4-[(7-methoxy-1,2,3,4-tetrahydro-naphthalen-2-yl)-propyl-amino]-piperidin-1-yl}-methanone 25, [M+H]⁺=465;

{4-[(7-methoxy-1,2,3,4-tetrahydro-naphthalen-2-yl)-propyl-amino]-piperidin-1-yl}-(1-methyl-piperidin-4-yl)-methanone 26, [M+H]⁺=395; and {4-[(7-methoxy-1,2,3,4-tetrahydro-naphthalen-2-yl)-propyl-amino]-piperidin-1-yl}-piperidin-3-yl-methanone 27, [M+H]⁺=450.

Similarly, following the procedure described above in Example 1, but replacing 7-methoxy-3,4-dihydro-1H-naphthalen-2-one with 6,7-dimethoxy-3,4-dihydro-1H-naphthalen-2-one in Step 1 and using the appropriate acylating compounds in Step 4a or Step 4b, the following compounds were prepared:

{4-[(6,7-dimethoxy-1,2,3,4-tetrahydro-naphthalen-2-yl)-propyl-amino]-piperidin-1-yl}-piperidin-4-yl-methanone 28, [M+H]⁺=480;

{4-[(6,7-dimethoxy-1,2,3,4-tetrahydro-naphthalen-2-yl)-propyl-amino]-piperidin-1-yl}-morpholin-4-yl-methanone 29, [M+H]⁺=482;

{4-[(6,7-dimethoxy-1,2,3,4-tetrahydro-naphthalen-2-yl)-propyl-amino]-piperidin-1-yl}-piperazin-1-yl-methanone 30, [M+H]⁺=481;

4-[(6,7-Dimethoxy-1,2,3,4-tetrahydro-naphthalen-2-yl)-propyl-amino]-piperidine-1-carboxylic acid diethylamide 31, [M+H]⁺=468;

{4-[(6,7-dimethoxy-1,2,3,4-tetrahydro-naphthalen-2-yl)-propyl-amino]-piperidin-1-yl}-(4-methyl-piperazin-1-yl)-methanone 32, [M+H]⁺=495; and {4-[(6,7-dimethoxy-1,2,3,4-tetrahydro-naphthalen-2-yl)-propyl-amino]-piperidin-1-yl}-(1-methyl-piperidin-4-yl)-methanone 33, [M+H]⁺=494.

Example 2

{4-[(7-Bromo-1,2,3,4-tetrahydro-naphthalen-2-yl)-propyl-amino]-piperidin-1-yl}-piperidin-4-yl-methanone

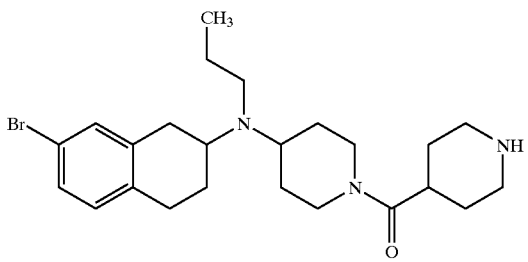

Step 1:
4-(7-Bromo-1,2,3,4-tetrahydro-naphthalen-2-ylamino)-piperidine-1-carboxylic Acid Tert-butyl Ester

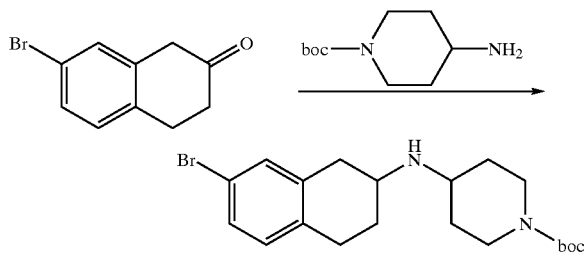

To a solution of 7-bromo-3,4-dihydro-1H-naphthalen-2-one (500 mg, 2.2 mmol) and 4-formyl-piperidine-1-carboxylic acid tert-butyl ester (445 mg, 2.2 mmol) in dichloroethane (50 mL) under a nitrogen atmosphere was added sodium triacetoxyborohydride (1.29 g, 5.55 mmol) in a single portion. The reaction was stirred at room temperature for 24 h. The reaction was concentrated in vacuo and partitioned between EtOAc (100 mL) and 5% aq. KOH (50 mL). The aqueous layer was extracted twice more with EtOAc (2×50 mL). The combined organic layers were washed with brine, dried over MgSO₄, filtered, and concentrated. Flash chromatography on silica gel eluting with 5% methanol/methylene chloride afforded 4-(7-bromo-1,2,3,4-tetrahydro-naphthalen-2-ylamino)-piperidine-1-carboxylic acid tert-butyl ester (610 mg).

Step 2:
4-[(7-Bromo-1,2,3,4-tetrahydro-naphthalen-2-yl)-propyl-amino]-piperidine-1-carboxylic Acid Tert-butyl Ester

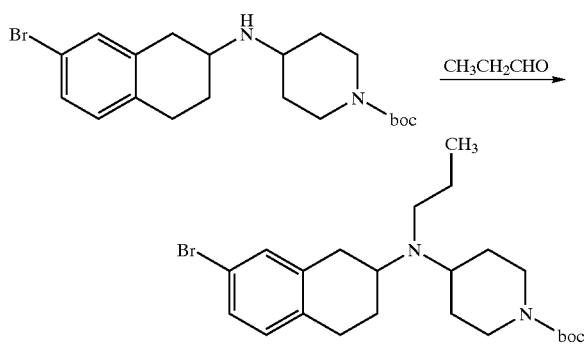

To a solution of 4-(7-bromo-1,2,3,4-tetrahydro-naphthalen-2-ylamino)-piperidine-1-carboxylic acid tert-butyl ester (610 mg, 1.5 mmol) and propionaldehyde (0.1 mL, 1.5 mmol) in dichloroethane (20 mL) under a nitrogen atmosphere was added sodium triacetoxyborohydride (795 mg, 3.75 mmol) in a single portion. The reaction was stirred at room temperature for 24 h then concentrated in vacuo. The residue was partitioned between EtOAc (75 mL) and 5% aq. KOH (50 mL). The aqueous phase was extracted twice more with EtOAc (2×30 mL). The combined organic layers were dried over MgSO₄, filtered, and concentrated onto silica (10 g). This was placed on top of a flash column and eluted with 20% hexanes in acetone. The fractions containing product were pooled and concentrated to afford 4-[(7-bromo-1,2,3,4-tetrahydro-naphthalen-2-yl)-propyl-amino]-piperidine-1-carboxylic acid tert-butyl ester (587 mg).

Step 3:
(7-Bromo-1,2,3,4-tetrahydro-naphthalen-2-yl)-piperidin-4-yl-propyl-amine

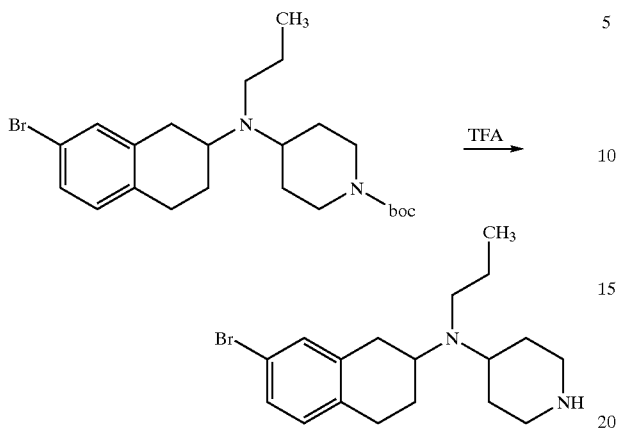

To a solution of 4-[(7-bromo-1,2,3,4-tetrahydro-naphthalen-2-yl)-propyl-amino]-piperidine-1-carboxylic acid tert-butyl ester (347 g, 0.77 mmol) in methylene chloride (30 mL) under a nitrogen atmosphere was added trifluoroacetic acid (10 mL). The reaction was stirred at room temperature for 30 min., and concentrated in vacuo. The residue was partitioned between EtOAc (50 mL) and 10% aq. KOH (50 mL). The organic layer was separated, dried over MgSO$_4$, filtered, and concentrated to afford (7-bromo-1,2,3,4-tetrahydro-naphthalen-2-yl)-piperidin-4-yl-propyl-amine (203 mg).

Step 4:
{4-[(7-Bromo-1,2,3,4-tetrahydro-naphthalen-2-yl)-propyl-amino]-piperidin-1-yl}-pyrrolidin-1-yl-methanone

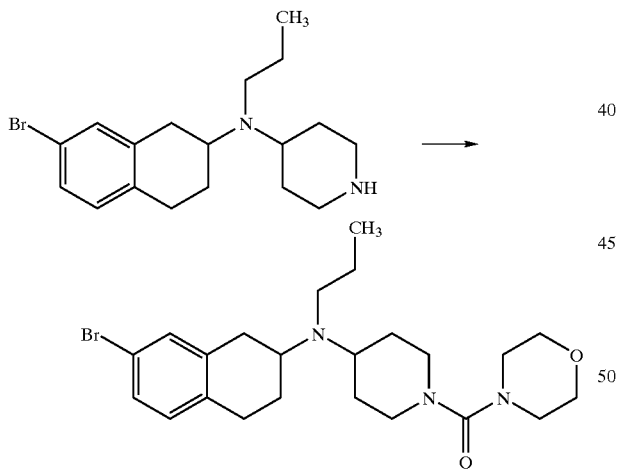

To a solution of the (7-bromo-1,2,3,4-tetrahydro-naphthalen-2-yl)-piperidin-4-yl-propyl-amine (200 μL of 0.25 M in dichloromethane, 50 μmol) was added 220 μL of 0.25 M solution of morpholine 4-carbonyl chloride in dichloromethane and 30 μL of DIEA. The reaction was stirred at 25° C. for 24 h. Concentrated in vacuo. The final product was isolated by preparative RPHPLC (YMC Combiprep ODS-A column, 10–90% acetonitrile: water (0.1% TFA)) to afford {4-[(7-bromo-1,2,3,4-tetrahydro-naphthalen-2-yl)-propyl-amino]-piperidin-1-yl}-pyrrolidin-1-yl-methanone 34 (4.6 mg), [M+H]$^+$=562.

Similarly following the procedure described above in Example 2 but replacing in Step 4 morpholine-4-carbonyl chloride with the appropriate carbonyl chlorides, the following additional compounds were prepared:

{4-[(7-bromo-1,2,3,4-tetrahydro-naphthalen-2-yl)-propyl-amino]-piperidin-1-yl}-piperidin-4-yl-methanone 35, [M+H]$^+$=499;

{4-[(7-bromo-1,2,3,4-tetrahydro-naphthalen-2-yl)-propyl-amino]-piperidin-1-yl}-((3R,5S)-3,5-dimethyl-piperazin-1-yl)-methanone 36, [M+H]$^+$=606;

4-[(7-bromo-1,2,3,4-tetrahydro-naphthalen-2-yl)-propyl-amino]-piperidin-1-yl}-morpholin-4-yl-methanone 37, [M+H]$^+$=478; and 4-[(7-bromo-1,2,3,4-tetrahydro-naphthalen-2-yl)-propyl-amino]-piperidine-1-carboxylic acid dimethylamide 38, [M+H]$^+$=543.

Example 3

{4-[((R)-7-Methoxy-1,2,3,4-tetrahydro-naphthalen-2-yl)-propyl-amino]-piperidin-1-yl}-piperidin-4-yl-methanone

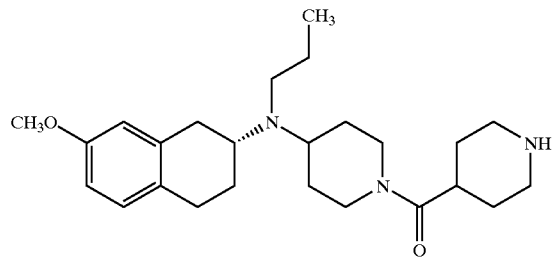

Step 1:
4-((R)-7-Methoxy-1,2,3,4-tetrahydro-naphthalen-2-ylamino)-piperidine-1-carboxylic Acid Tert-butyl Ester

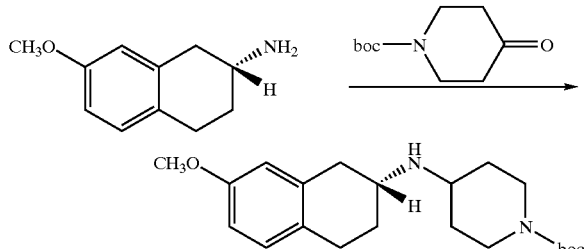

To a solution of (R)-7-methoxy-1,2,3,4-tetrahydro-naphthalen-2-ylamine hydrochloride (6.0 g, 28.1 mmol) (prepared as described in the French patent FR 2,653,765 or available commercially) and 4-oxo-piperidine-1-carboxylic acid tert-butyl ester (6.7g, 33.7 mmol, 1.2 eq.) in dichloroethane (200 mL) under an inert atmosphere was added sodium triacetoxyborohydride (14.9 g, 70.2 mmol, 2.5 eq). The reaction was stirred at room temperature for 24 h then concentrated in vacuo. The residue was partitioned between EtOAc (200 mL) and 5% KOH (150 mL). The aqueous layer was extracted twice more with EtOAc (2×75 mL). The combined organic layers were dried (MgSO$_4$), filtered, and concentrated to afford 4-((R)-7-methoxy-1,2,3,4-tetrahydro-naphthalen-2-ylamino)-piperidine-1-carboxylic acid tert-butyl ester as a yellow oil (9.7 g).

Step 2:
((R)-7-Methoxy-1,2,3,4-tetrahydro-naphthalen-2-yl)-piperidin-4-yl-propyl-amine

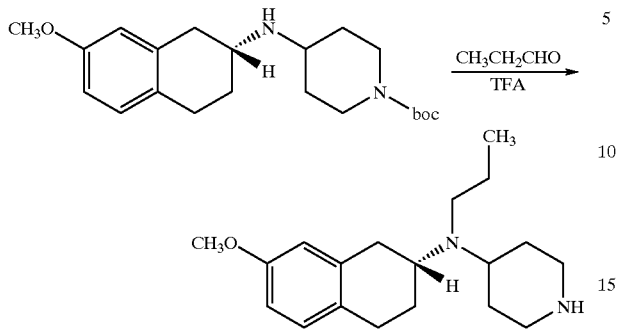

To a solution of 4-((R)-7-methoxy-1,2,3,4-tetrahydro-naphthalen-2-ylamino)-piperidine-1-carboxylic acid tert-butyl ester (9.7g, 23.4 mmol) and propionaldehyde (2.0 mL, 28.1 mmol) in dichloroethane (150 mL) under a nitrogen atmosphere was added sodium triacetoxyborohydride (10.9 mg, 51.5 mmol) in a single portion. The reaction was stirred at room temperature for 24 h then concentrated in-vacuo. The residue was partitioned between EtOAc (175 mL) and 5% aq. KOH (150 mL). The aqueous phase was extracted twice more with EtOAc (2×30 mL). The combined organic layers were dried over MgSO₄, filtered, and concentrated to afford 10.0 g of the protected amine, which was treated with trifluoroacetic acid as described herein to afford ((R)-7-methoxy-1,2,3,4-tetrahydro-naphthalen-2-yl)-piperidin-4-yl-propyl-amine (7.0 g).

Step 3:
{4-[((R)-7-Methoxy-1,2,3,4-tetrahydro-naphthalen-2-yl)-propyl-amino]-piperidin-1-yl}-piperidin-4-yl-methanone

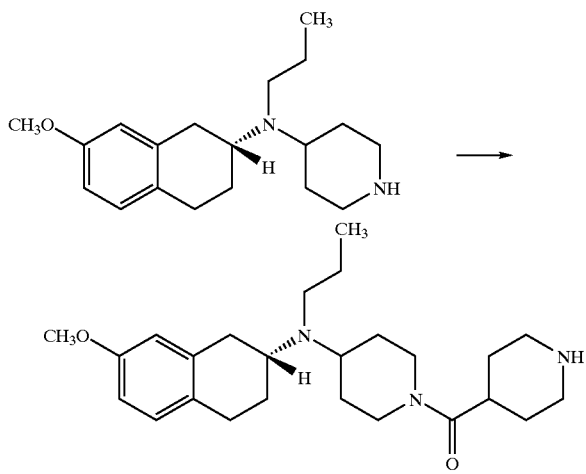

Under an inert atmosphere was combined ((R)-7-methoxy-1,2,3,4-tetrahydro-naphthalen-2-yl)-piperidin-4-yl-propyl-amine (7.0 g, 23.14 mmol), piperidine-1,4-dicarboxylic acid mono-tert-butyl ester (5.3 g, 23.14 mmol), EDCI (4.43 g, 23.14 mmol), HOBT (3.13 g, 23.14 mmol), and triethylamine (65 mL, 46.3 mmol) in dichloromethane (140 mL). The mixture was stirred at room temperature for 48 h then concentrated in vacuo. The residue was taken-up in EtOAc (150 mL) and washed with water (100 mL), 1N NaOH (30 mL), and brine (30 mL), then dried (MgSO₄). The solution was filtered, and concentrated. This was flash chromatographed on silica gel eluting with 20% acetone in hexanes to afford the protected amine (10.0 g), which was deprotected with 10 mL trifluoroacetic acid as described herein to afford {4-[((R)-7-methoxy-1,2,3,4-tetrahydro-naphthalen-2-yl)-propyl-amino]-piperidin-1-yl}-piperidin-4-yl-methanone 39 (6.5 g ), [M+H]⁺=450.

Example 4

2-Chloro-benzenesulfonic acid 7-{[1-(mornholine-4-carbonyl)-piperidin-4-yl]-propyl-amino}-5,6,7,8-tetrahydro-naphthalen-2-yl Ester

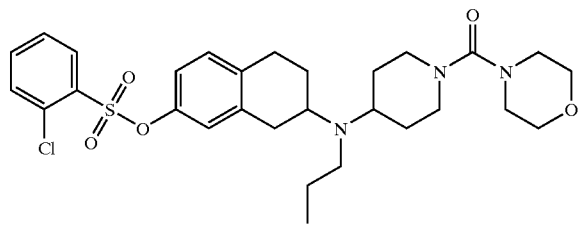

Step 1:
{4-[7-Methoxy-1,2,3,4-tetrahydro-naphthalen-2-yl)-propyl-amino]-piperidin-1-yl}-morpholin-4-yl-methanone

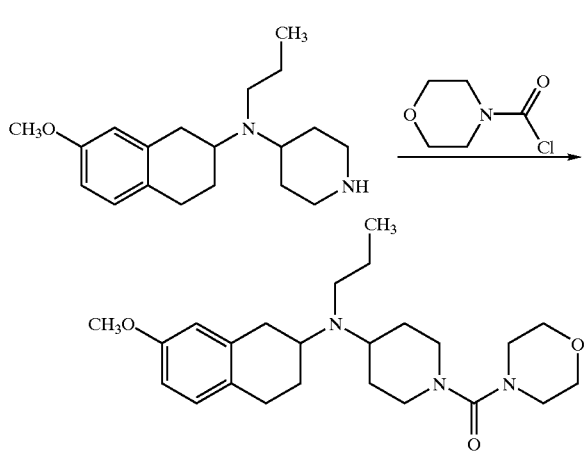

To an ice-cold solution of (7-methoxy-1,2,3,4-tetrahydro-naphthalen-2-yl)-piperidin-4-yl-propyl-amine (1.0 g, 3.3 mmol) and triethylamine (0.5 ml, 3.6 mmol) under an inert atmosphere was added morpholine-4-carbonyl chloride (0.4 mL, 3.5 mmol) dropwise. The ice bath was removed and the reaction stirred at room temperature for 4 h. The methylene chloride was washed 2 times with water (30 mL), dried (MgSO₄), filtered, and concentrated to afford {4-[(7-methoxy-1,2,3,4-tetrahydro-naphthalen-2-yl)-propyl-amino]-piperidin-1-yl}-morpholin-4-yl-methanone as an oil (1.16 g).

Step 2:
{4-[(7-Hydroxyl-1,2,3,4-tetrahydro-naphthalen-2-yl)-propyl-amino]-piperidin-1-yl}-morpholin-4-yl-methanone

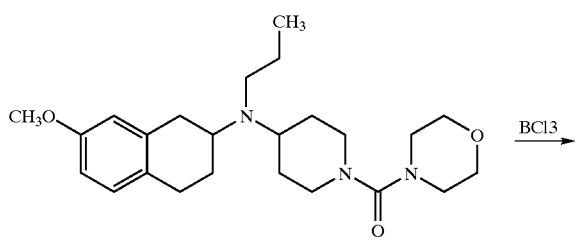

-continued

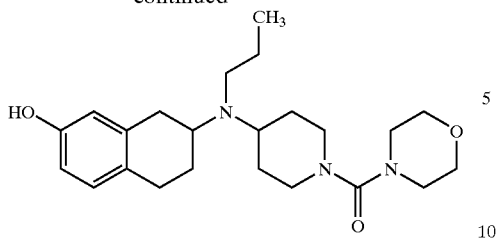

To a −78° C. solution of {4-[(7-methoxy-1,2,3,4-tetrahydro-naphthalen-2-yl)-propyl-amino]-piperidin-1-yl}-morpholin-4-yl-methanone (300 mg, 0.72 mmol) and tetrabutylammonium iodide (292 mg, 0.79 mmol) in dichloromethane (20 mL) under an inert atmosphere was added boron trichloride (1M, 2.5 mL, 2.5 mmol) dropwise. The reaction was warmed to room temperature and stirred for 2.5 h. The reaction was quenched by slow addition of water and the organic layer separated and dried (MgSO$_4$). This was concentrated onto silica (1.5 g) and placed on top of a flash column. Chromatography eluting with 30% acetone in hexanes afforded {4-[(7-hydroxy-1,2,3,4-tetrahydro-naphthalen-2-yl)-propyl-amino]-piperidin-1-yl}-morpholin-4-yl-methanone (128 mg).

Step 3:
2-Chloro-benzenesulfonic Acid 7-{[1-(morpholine-4-carbonyl)-piperidin-4-yl]-propyl-amino}-5,6,7,8-tetrahydro-naphthalen-2-yl Ester

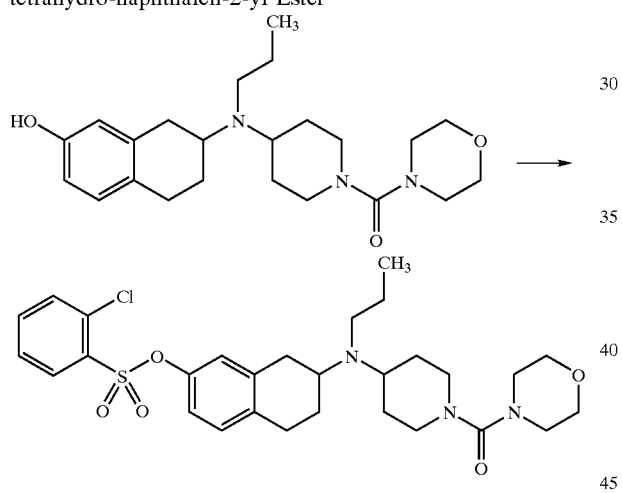

To a solution of {4-[(7-hydroxy-1,2,3,4-tetrahydro-naphthalen-2-yl)-propyl-amino]-piperidin-1-yl}-morpholin-4-yl-methanone (50 µmole in 420 µL DCM) was added 30 µL of DIEA followed by 220 µL of a 0.25M solution of 2-chlorobenzenesulfonyl chloride in THF. The solution was allowed to stir for 24 h at 25° C. under N$_2$. Concentrated in vacuo. The final product was isolated by preparative RPHPLC (YMC Combiprep ODS-A column, 10–90% acetonitrile: water (0.1% TFA)) to afford 2-Chloro-benzenesulfonic acid 7-{[1-(morpholine-4-carbonyl)-piperidin-4-yl]-propyl-amino}-5,6,7,8-tetrahydro-naphthalen-2-yl ester 40 (5.1 mg), [M+H]$^+$=690.

Similarly, following the procedure described above in Example 4, but replacing 2-chlorobenzene sulfonyl chloride with the appropriate sulfonyl chlorides, the following compounds were prepared:

2,5-dichloro-thiophene-3-sulfonic acid 7-{[1-(morpholine-4-carbonyl)-piperidin-4-yl]-propyl-amino}-5,6,7,8-tetrahydro-naphthalen-2-yl ester 41, [M+H]$^+$=731;

2-bromo-benzenesulfonic acid 7-{[1-(morpholine-4-carbonyl)-piperidin-4-yl]-propyl-amino}-5,6,7,8-tetrahydro-naphthalen-2-yl ester 42, [M+H]$^+$=735;

2-cyano-benzenesulfonic acid 7-{[1-(morpholine-4-carbonyl)-piperidin-4-yl]-propyl-amino}-5,6,7,8-tetrahydro-naphthalen-2-yl ester 43, [M+H]$^+$=681; and 3,5-dimethyl-isoxazole-4-sulfonic acid 7-{[1-(morpholine-4-carbonyl)-piperidin-4-yl]-propyl-amino}-5,6,7,8-tetrahydro-naphthalen-2-yl ester 44, [M+H]$^+$=675.

Example 5

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 6

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 7

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Example 8

Parenteral Formulation (IV)

| Ingredient | % wt./wt. |
|---|---|
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 9

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 10

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 11

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 12

Radioligand Binding Studies

The inhibitory activity of compounds of this invention in vitro was determined using a modification of the method described in Hegde, S. S. et al. 1997 *Br. J. Pharmacol.*, 120, 1409–1418.

Cell membranes from Chinese hamster ovary cells expressing the recombinant human muscarinic receptors ($m_1$–$m_5$) were employed. The assays were conducted with the radioligand [$^3$H]N-methyl scopolamine(0.4 nM, specific activity 84 Ci.mmol$^{-1}$) in a final volume of 0.25 mL Tris-Krebs buffer. Non-specific binding was defined with 1 $\mu$M atropine. Assays were performed using scintillation proximity assay technology. Competition-displacement curves were generated using 10 concentrations of test compounds and were analyzed by iterative curve fitting to a four parameter logistic equation. p$IC_{50}$ values (-log of the $IC_{50}$) were converted to pKi values using the Cheng-Prusoff equation.

Compound of this invention were active in this assay. Representative values for the M2 and M3 receptor are shown below.

| Structure | Cpd # | Ex | m2/ | m3 |
|---|---|---|---|---|
| 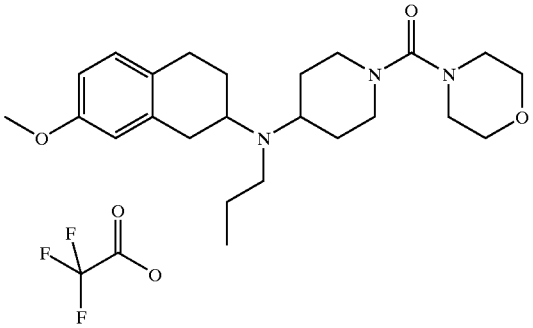 | 1 | 1 | 8.57 | 8.83 |

-continued

| Structure | Cpd # | Ex | m2/ | m3 |
|---|---|---|---|---|
| (structure) | 3 | 1 | 7.38 | 7.31 |
| (structure) | 4 | 1 | 7.58 | 7.29 |
| (structure) | 5 | 1 | 8.50 | 8.23 |
| (structure) | 15 | 1 | 8.37 | 8.17 |
| (structure) | 16 | 1 | 9.01 | 8.80 |

-continued

| Structure | Cpd # | Ex | m2/ | m3 |
|---|---|---|---|---|
| (structure with Cl, dimethoxy-tetrahydronaphthalene, propyl, piperidine-piperidine carbonyl) | 28 | 1 | 8.30 | 7.94 |
| (structure with methoxy-tetrahydronaphthalene, Cl, propyl, piperidine, N-methylpiperazine carbonyl) | 23 | 1 | 9.24 | 8.56 |
| (structure with Br-tetrahydronaphthalene, Cl, propyl, piperidine-piperidine carbonyl) | 35 | 2 | 8.74 | 9.05 |
| (Chiral; structure with Cl, methoxy-tetrahydronaphthalene, propyl, piperidine-piperidine carbonyl) | 39 | 3 | 8.66 | 9.02 |

Example 13

Oxotremorine/Pilocarpine-Induced Salivation (OIS/PIS) Model in Anesthetized Rats.

Female Sprague-Dawley rats (Charles-River, 200–300 g) rats were anesthetized with urethane (1.5 g/kg, sc) and were tracheotomized. One femoral vein was cannulated for drug administration. After a one hour stabilization period, rats were pre-treated with methoctramine (only for OIS) to antagonize $M_2$ receptor mediated bradycardia. Each animal was dosed, intravenously, with a single dose of the vehicle or the reference compound. Ten minutes later, pre-weighed cotton pads were placed in the animals mouth following which they were dosed with vehicle or oxotremorine (0.1 mg/kg, iv)/pilocarpine (1 mg/kg, iv). Fresh cotton pads were placed at 5 minutes post-oxotremorine/pilocarpine and saliva collected for an additional 5 minutes. The cotton pads (5 and 10-minute period) were then re-weighed to determine the amount of saliva secreted during the 10-minute period.

All oxotremorine/pilocarpine treated groups were compared using one-way analysis of variance. Pair-wise comparisons were made using Dunnett's test. The ranked data (non-parametric technique) or actual levels of the data (parametric technique) are applied in the analysis depending upon the results of the Bartlett's test, which tests homogeneity of variances. The vehicle/oxotremorine group and vehicle/pilocarpine was compared to the vehicle/vehicle group using Wilcox on rank-sum test. An estimate of the $ID_{50}$ for each compound with respect to the 10 minute overall secretion weight for each animal was obtained. The sigmoidal model is in the form of $$Resp = min + (max - min)/(1 + (dose/ID_{50})^{**}N)$$

where $ID_{50}$ is the dose to achieve half the maximal response, N is the curvature parameter and max is the max response for the dose response curve. The minimum response was fixed at 0 in the model.

Compounds of this invention were active in this assay.

Example 14

Inhibition of Volume-Induced Contractions in Rats

The muscarinic receptor inhibitory activity of compounds of this invention in vivo was determined in rats using a modification of the method described in Hegde, S. S. et al. 1996, *Proceedings of the 26th Annual Meeting of the International Continence Society* (August 27th–30th), Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a positive control.

Compounds of this invention were active in this assay.

Example 15

Anti-muscarinic Activity in Anesthetized Dogs

The muscarinic receptor inhibitory activity of compounds of this invention in vivo was determined in dogs using a modification of the method described in Newgreen, D. T. et al. 1996, *J. Urol.*, 155 (Suppl. 5), 1156.

Female beagles (Marshall Farms, North Rose, N.Y.) were fasted for 18 hours prior to the experiment; water was allowed ad libitum. On the day of the experiment, dogs were anesthetized and maintained on pentobarbital (36 mg/kg, iv initially, then 5–10 mg/kg, iv for maintenance). Intravenous fluids were also administered to the dog for the remainder of the experiment. The dogs were artificially ventilated, via an endotracheal tube, with an Harvard respirator (Model 613). Both femoral veins and one femoral artery was cannulated for drug administration and blood pressure measurement, respectively. Blood pressure was measured with a Gould transducer (Model P23XL) and recorded on a Gould recorder (Model 3400). A sublingual incision was made to expose the left mandibular duct, which was then cannulated for the collection of saliva into pre-weighed vials. The left salivary gland was exposed via a submandibular incision. The chorda-lingual nerve was isolated and had a bipolar electrode placed on it for stimulation. Test responses to chorda-lingual nerve stimulation were obtained to confirm proper electrode placement.

After completion of surgery, physostigmine (180 µg/kg/h, iv) (a cholinesterase inhibitor) was infused for the remainder of the experiment. Following a one hour stabilization period, two control chorda-lingual nerve stimulations were performed at 12 Hz, 10 V, 0.5 ms duration (Grass S48). The chorda-lingual nerve was stimulated for 20 seconds and 2 minutes, respectively, with a minimum of 10 minute interval between each set of stimulations. After two consistent control responses were obtained, the vehicle or the reference compound was dosed in a cumulative fashion, 3 minutes prior to each stimulation of the chorda-lingual nerve. Experiments in which consistent salivation responses could not be obtained were not included in the analysis. Atropine (1.0 mg/kg, iv) was given as a positive control at the end of the study.

Mean arterial blood pressure was calculated as Diastolic arterial pressure+(Systolic arterial pressure—Diastolic arterial pressure)/3. Heart rate was derived from the pressure pulse. Saliva was collected in pre-weighed vials and weighed after each collection to determine the volume of saliva secreted. Inhibition of salivary gland responses were expressed as a percent of the effect of atropine (1 mg/kg, iv).

$ED_{50}$ Estimation

For % max inhibition salivation, parameter estimation was performed using a nonlinear mixed model. The method was implemented using PROC NLIN initially and PROC MIXED iteratively. This procedure assumed the following sigmoidal dose-response model:

$$\text{Response} = \text{Min} + \frac{\text{Max} - \text{Min}}{1 + 10^{-\frac{(x-\mu)}{\sigma}}}$$

where response=% max inhibition bladder contraction at peak, $x = \log_{10}$ dose of treatment and the 4 parameters were: $\log_{10} ED50$ ($\mu$), maximum and minimum response (Max and Min), and curvature ($\sigma$). The minimum was assumed 0%. This method assumed compound symmetry for the covariance structure. It was an iterative curve-fitting procedure that accounted for the dependence between multiple measurements from the same animal, and estimated the desired parameters and their confidence limits by adjusting its error calculations to account for within subject correlation.

Baseline Comparisons

To compare each dose to baseline control for every variable, a two-way ANOVA with main effects of subject and treatment was performed, followed by a pair t-test at each dose level. If the overall treatment effect was not significant (p-value>0.05) in ANOVA, a Bonferroni adjustment for p-values was used for the p-value of pair t-test at each dose.

Compounds of this invention were active in this assay.

Example 16

In Vivo Antimuscarinic Activity in Bronchoconstriction Assays

Antagonist activity is assessed against methacholine-induced bronchoconstriction and bradycardia in the anesthetized rat model following a procedure similar to that described by Hirose et al, 2001, *J. Pharm. Exp. Ther.*, Vol 297, 790–797. Compounds are given intravenously, orally or by intratracheal instillation prior to challenge with intravenous methacholine. Lung resistance and dynamic compliance are used as indices of bronchoconstriction.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. Compounds of Formula I:

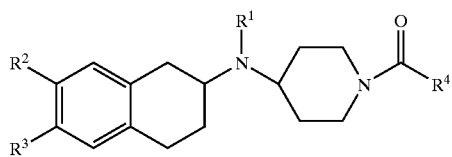

Formula I wherein:
R¹ is (C_{1-6})alkyl;
R² is halogen or —OR';
R³ is hydrogen or —OR';
R' is hydrogen, (C_{1-6})alkyl, or SO₂R";
R" is (C_{1-6})alkyl, haloalkyl, aryl or heteroaryl, wherein said aryl or heteroaryl groups are optionally substituted with a group selected from (C_16)alkyl, halo, haloalkyl, cyano, nitro, alkylsulfonyl, and alkylsulfonylamino;
R⁴ is (i) (C_{1-6})alkyl, (ii) aryl, heterocyclyl, or heteroaryl, wherein said aryl, heterocyclyl or heteroaryl groups are optionally substituted with a group selected from (C_{1-6}) alkyl, halo, haloalkyl, (C_{1-6})alkoxy, cyano, amino, mono- or di alkylamino, nitro, alkylsulfonyl, alkylcarbonyl, urea, alkylcarbonylamino, alkylsulfonylamino, alkylaminosulfonyl, alkoxycarbonyl, heterocyclyl and heteroaryl, or (iii) —NR⁵R⁶; and
R⁵ and R⁶ are independently of each other hydrogen, (C_{1-6})alkyl, aryl or heterocyclyl; wherein said aryl or heterocyclyl groups are optionally substituted with (C_{1-6})alkyl, halo, haloalkyl, cyano, (C_{1-6})alkoxy, and alkylsulfonyl;
or an individual isomer, a racemic or non-racemic mixture of isomers, or an acceptable salt or solvate thereof.

2. The compound of claim 1, wherein R² is (C_{1-6})alkoxy and R³ is hydrogen.
3. The compound of claim 1, wherein R² is (C_{1-6})alkoxy and R³ is (C_{1-6})alkoxy.
4. The compound of claim 1, wherein R² is —OSO₂R" and R³ is hydrogen.
5. The compound of claim 1, wherein R² is hydroxy and R³ is hydrogen.
6. The compound of claim 1, wherein R² is halogen and R³ is hydrogen.
7. The compound of claim 1 wherein R⁴ is (C_{1-6})alkyl.
8. The compound of claim 7, wherein R¹ is ethyl or propyl.
9. The compound of claim 8, wherein R² is —OR', and R³ is —OR' or hydrogen.
10. The compound of claim 1, wherein R⁴ is an aryl group.
11. The compound of claim 10, wherein R⁴ is phenyl optionally substituted with a group selected from (C_{1-6}) alkyl, halo, haloalkyl, (C_{1-6})alkoxy, cyano, amino, mono- or di alkylamino, nitro, alkylsulfonyl, alkylcarbonyl, urea, alkylcarbonylamino, alkylsulfonylamino, alkylaminosulfonyl, alkoxycarbonyl, heterocyclyl and heteroaryl.
12. The compound of claim 10, wherein R¹ is ethyl or propyl.
13. The compound of claim 11, wherein R¹ is ethyl or propyl.
14. The compound of claim 13, wherein R² is —OR', and R³ is —OR' or hydrogen.
15. The compound of claim 1, wherein R⁴ is a heteroaryl group.

16. The compound of claim 15, wherein R⁴ is selected from furanyl, thiophenyl, isooxazolyl, oxazolyl, imidazolyl, and pyrazolyl, all optionally substituted with one or two (C_{1-6}) alkyl.
17. The compound of claim 15, wherein R¹ is ethyl or propyl.
18. The compound of claim 16, wherein R¹ is ethyl or propyl.
19. The compound of claim 18, wherein R² is —OR', and R³ is —OR' or hydrogen.
20. The compound of claim 1, wherein R⁴ is a heterocyclyl group.
21. The compound of claim 20, wherein R⁴ is piperidinyl, pyrrolidinyl, morpholinyl, piperazinyl, or diazepanyl, all optionally substituted with one or two (C_{1-6})alkyl or alkylcarbonyl groups.
22. The compound of claim 20, wherein R⁴ is piperidin-4-yl, optionally substituted with one or two (C_{1-6})alkyl groups or alkylcarbonyl groups.
23. The compound of claim 20, wherein R⁴ is piperidin-1-yl, optionally substituted with one or two (C_{1-6})alkyl groups.
24. The compound of claim 20, wherein R⁴ is pyrrolidin-1-yl, optionally substituted with one or two (C_{1-6})alkyl groups.
25. The compound of claim 20, wherein R⁴ is [1,4]-diazepany-1-yl, optionally substituted with one or two (C_{1-6})alkyl groups.
26. The compound of claim 20, wherein R⁴ is piperazin-1-yl, optionally substituted with one or two (C_{1-6})alkyl groups.
27. The compound of claim 20, wherein R⁴ is morpholinyl, optionally substituted with one or two (C_{1-6}) alkyl groups.
28. The compound of claim 20, wherein R¹ is ethyl or propyl.
29. The compound of claim 21, wherein R¹ is ethyl or propyl.
30. The compound of claim 29, wherein R² is —OR', and R³ is —OR' or hydrogen.
31. The compound of claim 1, wherein R⁴ is —NR⁵R⁶.
32. The compound of claim 31, wherein R⁵ is (C_{1-6})alkyl, and R⁶ is hydrogen or (C_{1-6})alkyl.
33. The compound of claim 31, wherein R¹ is ethyl or propyl.
34. The compound of claim 33, wherein R² is —OR', and R³ is —OR' or hydrogen.
35. The compound of claim 1, comprising:
{4-[(7-methoxy-1,2,3,4-tetrahydro-naphthalen-2-yl)-propyl-amino]-piperidin-1-yl}-piperazin-1-yl-methanone;
{4-[(7-methoxy-1,2,3,4-tetrahydro-naphthalen-2-yl)-propyl-amino]-piperidin-1-yl}-morpholin-4-yl-methanone;
{4-[(6,7-dimethoxy-1,2,3,4-tetrahydro-naphthalen-2-yl)-propyl-amino]-piperidin-1-yl}-piperidin-4-yl-methanone;
{4-[((R)-7-methoxy-1,2,3,4-tetrahydro-naphthalen-2-yl)-propyl-amino]-piperidin-1-yl}-piperidin-4-yl-methanone;
1-{4-[(7-methoxy-1,2,3,4-tetrahydro-naphthalen-2-yl)-propyl-amino]-piperidin-1-yl}-ethanone;
{4-[(6,7-dimethoxy-1,2,3,4-tetrahydro-naphthalen-2-yl)-propyl-amino]-piperidin-1-yl}-piperazin-1-yl-methanone;
{4-[(7-methoxy-1,2,3,4-tetrahydro-naphthalen-2-yl)-propyl-amino]-piperidin-1-yl}-(4-methyl-piperazin-1-yl)-methanone; and
{4-[(7-Bromo-1,2,3,4-tetrahydro-naphthalen-2-yl)-propyl-amino]-piperidin-1-yl}-piperidin-4-yl-methanone.

36. A pharmaceutical composition comprising a therapeutically effective amount of a compound of claim 1 in admixture with an acceptable carrier.

37. The pharmaceutical composition of claim 36, wherein the compound is suitable for administration to a subject having a disease state which is alleviated by treatment with a M2/M3 muscarinic receptor antagonist.

38. A method of treating a subject which comprises administering to the subject with a disease treatable with a M2/M3 muscarinic antagonist a therapeutically effective amount of one or more compounds of claim 1.

39. The method of claim 38, wherein the disease state is associated with smooth muscle disorders comprising diseases of the genitourinary or gastrointestinal tract, or of respiratory states.

40. The method of claim 39, wherein the disease state is associated with the genitourinary tract.

41. The method of claim 40, wherein the disease state comprises overactive bladder, detrusor hyperactivity, urgency, frequency, reduced bladder capacity, incontinence episodes, changes in bladder capacity, micturition threshold, unstable bladder contractions, sphincteric spasticity, outlet obstruction, outlet insufficiency, pelvic hypersensitivity, idiopathy conditions, or detursor instability.

42. The method of treatment of claim 39, wherein the disease state comprises respiratory states.

43. The method of treatment of claim 42, wherein the disease state comprises respiratory states from allergies or asthma.

44. The method of treatment of claim 39, wherein the disease state comprises gastrointestinal tract disorders.

45. A process for preparing a compound as claimed in claim 1 which process comprises reacting a compound having a general formula d:

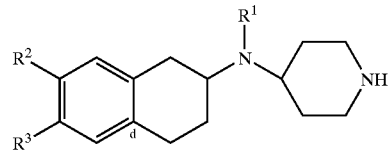

wherein $R^1$, $R^2$ and $R^3$ are as described in claim 1, with a compound of general Formula $R^4C(O)L$, wherein L is a leaving group and $R^4$ is as described in claim 1, to prepare a compound of Formula I

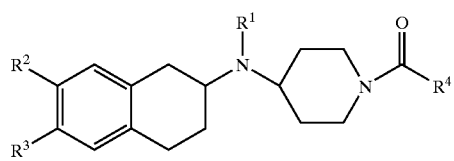

wherein $R^1$, $R^2$, $R^3$ and $R^4$ are as described in claim 1.

* * * * *